US006971381B2

(12) United States Patent
Langford

(10) Patent No.: US 6,971,381 B2
(45) Date of Patent: Dec. 6, 2005

(54) ACTUATION INHIBITOR FOR METERED DOSE INHALERS

(75) Inventor: Stanley C. Langford, 2681 Credit Valley Road, Mississauga, Ontario (CA), L5M 4J8

(73) Assignee: Stanley C. Langford, Mississauga (CA)

(*) Notice: Subject to any disclaimer, the term of this patent is extended or adjusted under 35 U.S.C. 154(b) by 93 days.

(21) Appl. No.: 10/345,480

(22) Filed: Jan. 17, 2003

(65) Prior Publication Data

US 2004/0139964 A1 Jul. 22, 2004

(51) Int. Cl.⁷ .............................................. A61M 11/00
(52) U.S. Cl. .......................... 128/200.23; 222/153.13; 221/154
(58) Field of Search ................ 128/200.23, 200.14; 285/305; 222/153.13, 162; 239/DIG. 14, 359; 24/16 R, 437, 455, 530, 537, 545, 563, 339, 30.5 P; 248/231.81, 230.7; 221/154

(56) References Cited

U.S. PATENT DOCUMENTS

| | | | |
|---|---|---|---|
| 3,001,524 A | 9/1961 | Maison et al. | |
| 3,154,281 A | * 10/1964 | Frank ........................ | 248/201 |
| 3,184,115 A | 5/1965 | Meshberg | |
| 3,370,815 A | * 2/1968 | Opperthauser ............. | 248/74.2 |
| 3,506,004 A | 4/1970 | Mann et al. | |
| 3,517,667 A | 6/1970 | Babbin et al. | |
| 3,521,332 A | 7/1970 | Kramer | |
| 3,622,053 A | 11/1971 | Ryden | |
| 3,799,448 A | * 3/1974 | Nozawa et al. ............. | 239/321 |
| 3,897,650 A | * 8/1975 | Pilston ....................... | 43/54.1 |
| 3,927,806 A | 12/1975 | Meshberg | |
| 4,130,116 A | 12/1978 | Cavazza | |
| 4,291,688 A | 9/1981 | Kistler | |
| 4,292,749 A | 10/1981 | Thomas | |

(Continued)

FOREIGN PATENT DOCUMENTS

| | | | |
|---|---|---|---|
| DE | 1 274 283 | 8/1968 | |
| EP | 1083131 A2 * | 3/2001 | ........... B65D/47/34 |
| WO | WO 97/06842 | 2/1997 | |

OTHER PUBLICATIONS

"Canister retention feature for inhalation device", Research Disclosure, Feb. 1995, No. 370.

*Primary Examiner*—Henry Bennett
*Assistant Examiner*—Mital Patel
(74) *Attorney, Agent, or Firm*—Marks & Clerk; Richard J. Mitchell

(57) ABSTRACT

An actuation inhibitor for metered dose inhalers comprises an annular band of semi-rigid plastics material having a substantially circular cross-section, with an upstanding wall encompassing from about 260° to 315°, a gap in the wall of from about 45° to 100°, and a pair of outwardly projecting walls, one at each side of the gap. The inside diameter when at rest in an unstressed manner is slightly smaller than that of a medication canister. The height is from about 40% to 65% of the predetermined diameter, and the length of each of the projecting walls is from about 10% to 50% of the height. The semi-rigid plastics material is sufficiently flexible to permit the pair of projecting walls to be spaced apart one from the other by up to about a further 90°, and the plastic memory permits the spreading apart of the projecting walls without being overcome.

11 Claims, 2 Drawing Sheets

U.S. PATENT DOCUMENTS

| | | | | |
|---|---|---|---|---|
| 4,320,832 A | * | 3/1982 | Edstrom | 206/228 |
| 4,377,106 A | * | 3/1983 | Workman et al. | 92/23 |
| 4,388,747 A | * | 6/1983 | Plummer | 24/535 |
| 4,441,633 A | * | 4/1984 | Bennett | 222/153.13 |
| 4,706,663 A | | 11/1987 | Makiej | |
| 4,817,822 A | | 4/1989 | Rand et al. | |
| 4,953,545 A | | 9/1990 | McCarty | |
| 4,997,148 A | * | 3/1991 | Sherman | 248/74.1 |
| 5,160,105 A | * | 11/1992 | Miller | 248/188.9 |
| 5,236,725 A | | 8/1993 | McCormack et al. | |
| 5,275,443 A | * | 1/1994 | Klinger | 285/82 |
| 5,505,192 A | | 4/1996 | Samiotes et al. | |
| 5,735,263 A | | 4/1998 | Rubsamen et al. | |
| 5,975,370 A | * | 11/1999 | Durliat | 222/153.06 |
| 6,116,234 A | | 9/2000 | Genova et al. | |
| 6,322,306 B1 | | 11/2001 | Dutton | |
| 6,352,181 B1 | * | 3/2002 | Eberhard et al. | 222/153.13 |
| 6,386,596 B1 | * | 5/2002 | Olson | 285/321 |
| 6,390,291 B1 | | 5/2002 | Garrill et al. | |

\* cited by examiner

ACTUATION INHIBITOR FOR METERED DOSE INHALERS

FIELD OF THE INVENTION

This invention relates to metered dose inhalers, and particularly it relates to an actuation inhibitor which precludes unintended or inadvertent actuation of the metered dose inhaler. The actuation inhibitor frictionally engages a metered dose medication canister when in place in a standardized L-shaped inhaler, and essentially comprises an annular band which is placed over the medication canister at the outer end thereof.

BACKGROUND OF THE INVENTION

Metered dose inhalers are well known. Regrettably, a large proportion of the population suffers from asthma and/or other respiratory diseases. Typically, such individuals rely on the use of inhalers in order to swiftly and accurately deliver medication through the mouth of the patient and windpipe to the lungs. Many such patients carry one or more inhalers with them at all times, and indeed many such patients sleep with inhalers very close at hand or even under their pillow. In most instances, especially with patients who are sufficiently mature—teenagers and above—they are entrusted to self-administer the appropriate medication. However, so as to reduce the chance of over- and under-medication, nearly all inhalers of the sort that permit self-administration of the medication do so in a metered fashion.

Moreover, so that such patients have ready access to their inhalers at all times, the inhalers are carried by the patients in such varied places and manners as their pockets, purses, tote bags, backpacks, briefcases, etc. This gives rise to a problem which, so far, has not been overcome. That is, if jostled or otherwise physically knocked about, metered dose inhalers may accidentally discharge their medication, one metered dose at a time. This comes as a consequence of the fact that the design which allows the inhaler to be deployed quickly also makes it vulnerable to being accidentally discharged while being transported. Moreover, the actuation valve in metered dose inhalers may sometimes be quite soft or easily depressed. Thus, it can sometimes happen that when the inhaler and its medication are necessary to be used, the medication or its propellant may have all been inadvertently expelled from the canister.

When it is necessary for patient to use a metered dose inhaler, typically the inhaler is removed from its storage place, a cap is removed from the mouthpiece, the inhaler is shaken, the mouthpiece is placed in the patient's mouth, with the canister in an upright position, and the upper end of the canister is depressed. That causes the actuation valve to open, and a metered amount of the medication contained within the canister is expelled therefrom into the mouth of the patient. By releasing a specific amount of the prescribed medication, the patient is able to alleviate or overcome the then existing symptoms. But of course, if all the medication that the patient expected to find in the canister has been inadvertently and accidentally dispelled as a consequence of the inhaler having been jostled, then serious and potentially grave circumstances may arise as they effect that patient.

The present inventor has unexpectedly discovered that accidental and inadvertent loss of medication from a metered dose inhaler may be precluded by the simple placement of an actuation inhibitor over the extending outer end of the medication canister when it is in place in an inhaler, in such a manner that the actuation inhibitor is frictionally engaged to the medication canister, so as to preclude sufficient downward movement of the canister within the inhaler such that the actuation valve may be actuated.

Typically, a metered dose inhaler, particularly those which are carried by patients to self-administration of the medication is entrusted, comprises an L-shaped inhaler body which has a mouthpiece for insertion into the mouth of the patient, and housing into which the medication canister is placed. The precise structure of such metered dose inhalers is beyond the scope of the present invention. Indeed, it must be recognized that there are many manufacturers who supply molded plastic inhaler bodies to the market, and there are many manufacturers who supply metered dose medication canisters to the market. While it is usually a fact that a particular manufacturer's inhaler body will be used with a particular medication—because, for example, they may have a specific color so as to indicate at a glance which medication is contained within the specific canister with which the inhaler body is being used—it is also possible that generic asthma medications, for example, may be used with generic metered dose inhaler bodies.

Other dispensers than metered dose inhalers may have means to preclude their inadvertent operation. For example, perfume nebulizers, soap dispensers, insect repellent sprays, cooking oil spray dispensers, and the like, have caps and/or collars which either cover a spray nozzle or surround the neck of the dispenser below the spray nozzle so as to physically preclude the nozzle being depressed. However, no such means have been provided up until the present invention which act to preclude inadvertent depression of a metered dose canister in a metered dose inhaler in such a manner that an unintended loss of medication will occur.

Specifically, there is nothing has been provided to the market which functions as an actuation inhibitor for metered dose inhalers, and which may be easily fitted to or removed from the medication canister; and which, at the same time, will permit actuation of the actuation valve of a metered dose inhaler in the event of a dire emergency. At the same time, the present invention provides such an actuation inhibitor which is of very low cost so that it can be provided to the patient each time a new metered dose inhaler is dispensed by a pharmacist, at little or no additional expense. Indeed, it is contemplated that in some circumstances, the outer surface of the actuation inhibitor may be employed to carry a simple warning, advertising material, or other written and/or graphic material which may be placed on or molded into the actuation inhibitor.

DESCRIPTION OF THE PRIOR ART

A number of prior art patents are known to the inventor. However, none of those patents appears to be significantly relevant to the present invention, insofar as they failed to disclose a structure such as that which is provided herein, and indeed most of the prior art patents do not discuss the issue of inadvertent and accidental loss of medication as a consequence of unintended actuation of the actuation valve in a metered dose inhaler.

MAISON et al U.S. Pat. No. 3,001,524 teaches an aerosol dispensing apparatus which is one of the first references to metered dose medication administration for purposes of inhalation therapy. However, the apparatus comprises a bottle or container which is inserted upwardly into the actuation end of a tube, with the other end of the tube in place in the patient's mouth. There is no housing for the medication container.

A similar metered dosage inhaler which employs a glass medication bottle that is fully enclosed within a housing, is taught in MESHBERG U.S. Pat. No. 3,184,115. That patent teaches a sealed construction which employs a structure that has a rotating locking sleeve located at the upper, valve end of the medication bottle. In that sense, it is noted that the this apparatus also operates in an upside-down manner relative to the manner in which present day metered dose inhalers which employ molded plastic bodies and metallic medication canisters operate.

MANN et al U.S. Pat. No. 3,506,004 teaches an inhalation device whose orientation is more in keeping with present day metered dose inhalers. A closed housing is employed, into which a replaceable aerosol container may be inserted. However, in this case, the mouthpiece is rotatable relative to the container housing; and when it is aligned with the container housing, a storage position for the dispenser is assumed.

The first apparent discussion of the use of a metallic canister in metered dose inhalers is found in CARVAZZA U.S. Pat. No. 4,130,116, which teaches an inhaler which can be carried in a box-like outer protective cover. Once again, the mouthpiece rotates into a functional orientation when one part of the box cover is slid lengthwise with respect to the other part. This also provides access to the canister for depression of the actuation valve.

A more modern appearance of a metered dose inhaler is taught in KISTLER U.S. Pat. No. 4,291,688. A separable skirt is provided for the mouthpiece, and a medication aerosol container is inserted into the skirt. The purpose of this inhalation device is to provide an audible signal when a metered dose is discharged through the mouthpiece to the patient A particle catcher for use with inhalation devices is taught in MAKIEJ U.S. Pat. No. 4,706,663. Its purpose is to reduce the velocity of aerosol medications as they are administered to the patient. To that end, the particle catcher is an adjunct to, and not a functional part of, a metered dose inhaler as they are typically dispensed by pharmacists.

U.S. Pat. No. 4,817,822 issued to RAND et al teaches an indicating device that is also used as an adjunct to the metered dose inhalers. The purpose, in this case, is to provide an indication to the patient as to the number of doses that have already been dispensed from the aerosol container, or as a number of doses which remain. The reason is that a patient may be surprised that all are nearly all of the medication has been dispensed; but the patent is silent as to the fact that the medication may have been accidentally dispensed.

Another adjunct device to be employed with metered dose inhalers—although in this case, the metered dose inhaler is illustrated as being used in an upside-down fashion—is taught in McCARTY U.S. Pat. No. 4,953,545. This patent teaches a dispersion chamber which is intended to be used with an otherwise conventional metered dose inhaler.

A United States patent which teaches a metered dose inhaler having an electronic counter is discussed in SAMIOTES el al U.S. Pat. No. 5,505,192. The counter is one of that can be placed over the end of any conventional medication aerosol canister, and functions to identify the quantity of medication that has been dispensed and therefore the status of the material which remains in the canister. The inventor herein is aware that this device won an award in 1998 for the "Asthma Breakthrough of the Year".

RUBSAMEN et al U.S. Pat. No. 5,735,263 is related to a metered dose inhaler where the medication to be dispensed is narcotic. The purpose of the invention is to provide a lockout device for controlled release of the narcotic formulation to the patient, whereby it is not possible for the patient to self-administer the medication except at predetermined timed intervals.

U.S. Pat. No. 6,116,234, issued to GENOVA et al, again teaches a metered dose inhaler which employs an agitator whereby the medication is thoroughly mixed so as to be homogenous when it is delivered to the patient.

A recently issued patent to GARRILL et al is U.S. Pat. No. 6,390,291, which teaches a method and package for storing a pressurized container. Specifically, the pressurized container which is discussed is a metered dose inhaler, and the package which is provided is intended particularly for metered dose inhalers which, since Jan. 1, 2003, have been mandated to be free of CFC. Such medications are adversely affected by moisture, and thus products will be shipped in a semi-permeable bag which allows it to breathe, while keeping out moisture. There is an admission that metered dose inhalers leak and can be accidentally discharged, but no solution to that problem is provided.

SUMMARY OF THE INVENTION

It is principally the purpose of present invention to provide a means whereby inadvertent and/or accidental actuation of a metered dose inhaler may be precluded, and yet to permit selective actuation of a metered dose inhaler even in the presence of the actuation inhibitor should such as an emergency situation arise.

To that end, the present invention provides an actuation inhibitor for metered dose inhalers, which comprises an annular band of semi-rigid plastics material having a substantially cylindrical configuration with a circular cross-section, and having an upstanding wall encompassing from about 260° to about 315°, a gap in the wall of from about 45° to about 100°, and a pair of outwardly projecting walls, one at each side of the gap.

The inside diameter of the cylindrical configuration when at rest in an unstressed manner is predetermined.

The height of the upstanding wall is from about 40% to about 65% of the predetermined diameter, and the length of each of the projecting walls is from about 10% to about 50% of the height.

The semi-rigid plastics material is sufficiently flexible to permit the pair of projecting walls to be spaced apart one from the other by an amount of up to about a further 90°.

Also, the semi-rigid plastics material has a plastic memory which permits the spreading apart of the projecting walls without overcoming the plastic memory.

Typically, the predetermined diameter is from about 75% to about 99% of a standardized diameter of the metered dose canisters intended for use in metered dose inhalers.

However, it is more usually from about 90% to about 95% of a standardized diameter of metered dose canisters intended for use in metered dose inhalers.

Also, the thickness of the upstanding wall and of the outwardly projecting walls is typically in the range of from about 10% to about 35% of the height thereof.

In any actuation inhibitor for metered dose inhalers in keeping with the present invention, the outwardly projecting walls may be substantially parallel one to the other.

However, in other embodiments of actuation inhibitors in keeping with the present invention, the projecting walls may extend radially outwardly from the respective sides of the gap.

Typically, the gap may extend for about 65° to about 80°, and the upstanding wall will encompass from about 280° to about 295°.

The present invention also provides for the combination of a standardized L-shaped inhaler body for use with a metered dose canister, a metered dose canister of medication to be inhaled through the mouth of the patient, and an actuation inhibitor for metered dose inhalers as described above.

In that case, the L-shaped inhaler comprises a mouthpiece to be placed in the mouth of a patient, and a canister housing into which a canister of medication is placed so is to have an actuating valve located near the junction of the housing and the mouthpiece. The canister extends above the housing when in an operating, vertical orientation; and the actuator inhibitor is placed over at least a portion of the canister where it extends above the housing so as to be frictionally engaged therewith.

Thus, when a force is applied to the canister so is to cause the canister to attempt to move within the housing towards the junction of the housing and the mouthpiece, the frictional engagement of the actuation inhibitor with the canister will be such that there will be an interference of the actuation inhibitor with at least a portion of the end of the housing remote from the junction, so as to thereby at least initially preclude actuation of the actuation valve.

Typically, the predetermined diameter of the actuation inhibitor, before its frictional engagement with the canister, is about 90% to about 95% of the diameter of the canister.

Moreover, the gap of the actuation inhibitor typically extends for about 68° to about 85° and the wall encompasses from about 275° to about 292°, when the actuation inhibitor has been frictionally engaged with the canister.

In another embodiment of the present invention, a different form of actuation inhibitor for metered dose inhalers is provided. Here, the actuation inhibitor takes the form of a cylindrical cap which has a closed first end and an open second end, and which is made from a plastics material which is frangible if pressure is placed on the cylindrical cap in an axial direction from the closed first end to the second open end.

The inside diameter of the cylindrical cap is predetermined, and so is the height of the cylindrical cap predetermined.

Typically, the predetermined diameter of the cylindrical cap may be from about 95% to about 110% of a standardized diameter of the metered dose canisters intended for use in metered dose inhalers.

Also, there may be at least three internally directed stiffening ribs which are formed on the inside surface of the cylindrical cap.

Is so, the predetermined diameter is from about 95% to about 99% of a standardized diameter of the metered dose canisters intended for use in metered dose inhalers, where the diameter is measured at a circle that is defined by the inner extremities of the stiffening ribs.

The present invention also provides for a metered dose inhaler which comprises an L-shaped body having a mouthpiece to be placed in the mouth of the patient and a canister housing into which a canister of medication is placed so as to have an actuating valve located near the junction of the housing and the mouthpiece.

The height of the housing is greater than the height of a canister of medication when in place in the housing, so that the top end of the housing is above the top end of a canister medication when in place in the housing.

There is a notch which is formed in the housing and which extends downwardly from the top end thereof in a location which is diametrically opposed to the mouthpiece.

Typically, the width of the notch is sufficient to accommodate a finger of the hand of a patient, so as to thereby permit actuation of the actuating valve by pressing downwardly on the top of the canister of medication when it is in place in the housing.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which.

DETAILED DESCRIPTION OF THE PREFERRED EMBODIMENTS

The novel features which are believed to be characteristic of the present invention, as to its structure, organization, use and method of operation, together with further objectives and advantages thereof, will be better understood from the following discussion.

Figure 1:
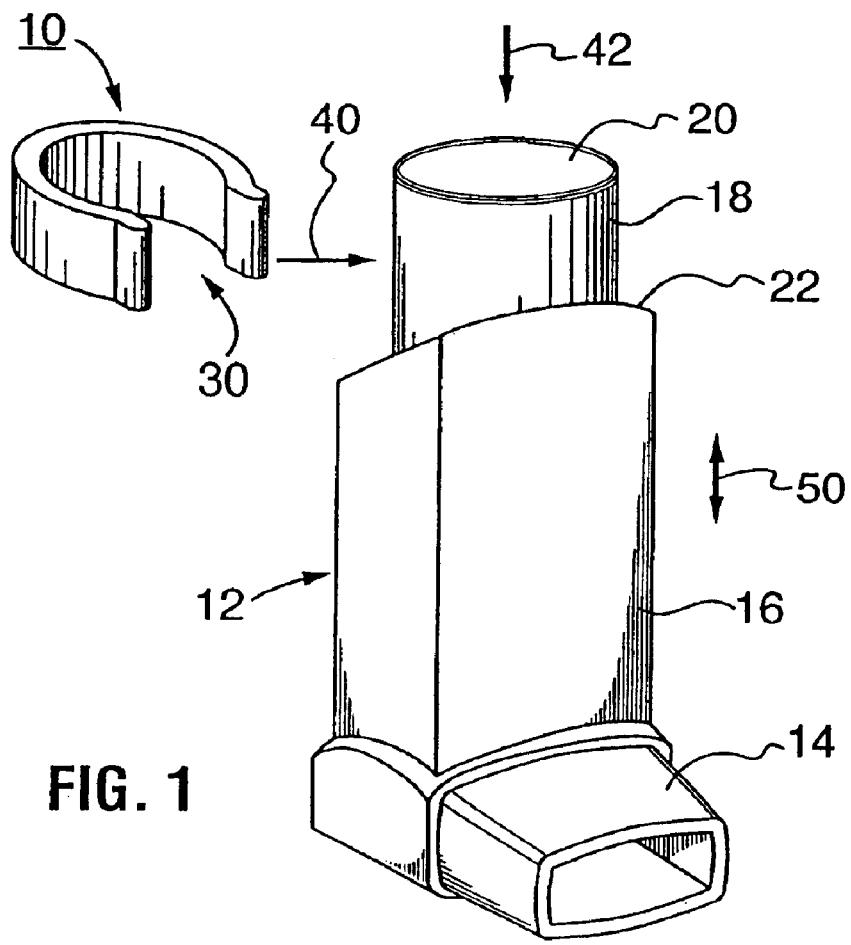
FIG. 1 is a perspective view of a typical metered dose inhaler and an actuation inhibitor in keeping with present invention, in its relationship to the metered dose inhaler.
Figure 2:
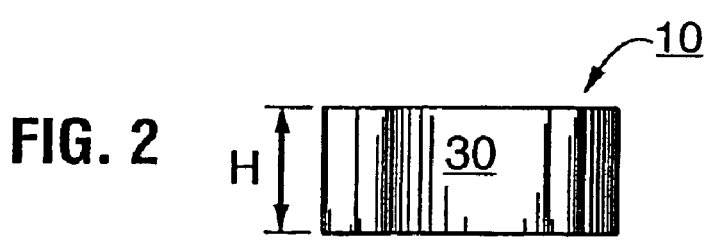
FIG. 2 is a an elevation of the actuation inhibitor of the present invention, seen from the open side thereof.
Figure 3:
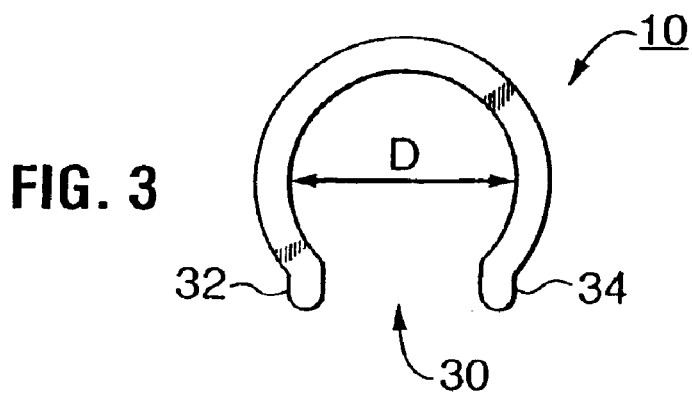
FIG. 3 is a plan view of the actuation inhibitor of the present invention.

An actuation inhibitor in keeping with the present invention is shown at 10 in each of FIGS. 1, 2, and 3. A typical metered dose inhaler is shown at 12 in FIG. 1. Elevation and plan views of the actuation inhibitor 10 are seen in FIGS. 2 and 3, respectively.

The typical metered dose inhaler 12 comprises a mouthpiece 14 and a housing 16. An aerosol canister 18 is placed into the housing 16 in the well-known manner; and actuation of the actuation valve of the medication canister 18 is effected by pushing down against the end 20 of the canister 18 in the direction shown by double-headed arrow 50, against a spring actuated valve at the lower end of the medication canister 18, also in the well-known manner. That actuation valve is, therefore, located in the region of the junction between the housing 16 and a mouthpiece 14.

Upon release of the pressure against the end 20 of the medication canister 18, the spring of the actuation valve will cause the canister 18 to move upwardly within the housing 16, also is indicated by the double-headed arrow 50. It does not matter how long the canister 18 is depressed against its actuation valve, only a predetermined, metered, dose of the medication found within the canister 18 will be dispensed from the canister and through the mouthpiece 14 to the mouth and thence to the lungs of the patient.

Typically, the end 20 of an aerosol medication canister is dished or concave so as to accommodate the fleshy underside of the end of the finger of the patient.

As has been discussed above, it may very often occur that inadvertent actuation of the actuation valve at the bottom end of the medication canister 18 will happen as a consequence of the assembled metered dose inhaler being jostled about in the pocket or purse, or elsewhere, of the patient who is carrying it. This happens quite often, as has been determined by the present inventor, with the result that when the patient is in some form of distress and may urgently require use of the medication contained within the canister 18 for purposes of inhalation therapy, the medication may no longer be present, at least in a useable or reliable quantity.

Typically, each metered dose inhaler contains more than 200 doses. However, to ensure the doses are consistent with one another and the quantity of the medication provided in each dose is consistent, the patient must agitate the puffer before using it so as to keep the medication in suspension with the propellant. Typically, in a medication leakage, either the active medicine or the propellant will be lost, and most likely not in equal proportion to one another. Thus, it is indeed possible that the patient may have discharged all the medication and be left with only the propellent. Conversely, the patient may have discharged all the propellent and be left with only the active medicine.

It will be seen and understood from a brief study of FIG. 1 that the actuation inhibitor 10 may be placed over the end of the canister 18 which extends above the end 22 of the housing 16. As will be discussed hereafter, the dimensional relationships of the actuation inhibitor 10 to the external diameter of the canister 18 are such that when the actuation inhibitor 10 is placed over the end of the canister 18, it will be frictionally engaged therewith.

Accordingly, it can be seen that there will be an interference between the bottom of the actuation inhibitor 10 and the top 22 of the housing 16, either at the front or side thereof, if there is any downward movement of the canister 18 towards the mouthpiece 14. That interference will preclude further downward movement of the canister 18 under most circumstances. It follows, therefore, that inadvertent dispensing of medication from the aerosol canister 18 will be precluded.

Referring briefly to FIGS. 2 and 3, certain dimensional relationships of the actuation inhibitor 10, in keeping with present invention, will be discussed. First, it will be seen that the actuation inhibitor comprises an annular band which has a substantially cylindrical configuration (see FIG. 1, in particular) having a circular cross-section as can be understood particularly from FIGS. 1 and 3. It will also be seen from each of the Figures that the configuration of the actuation inhibitor 10 is such that it is not entirely circular; that is, it does not enclose a full circle. Rather, there is a gap 30 which is such as to form an open side of the actuation inhibitor 10. The gap has a pair of outwardly projecting walls 32, 34 at each side thereof; and it will be seen particularly from FIGS. 1 and 2 that the annular band which comprises the actuation inhibitor 10 is an upstanding wall.

The nature of the upstanding wall is such that it encompasses from about 260° to about 315°; and therefore the gap 30 extends for about 45° to about 100°.

The material from which the actuation inhibitor 10 is molded is a semi-rigid plastics material such as polypropylene; other medically acceptable plastics materials may be employed, the choice of which is beyond the scope of present invention. However, the nature of the semi-rigid plastics material which is chosen must be such that it is sufficiently flexible to permit the pair of projecting walls 32, 34 to be spaced apart one from another by an amount of up to another 90°, and yet the material must have a plastic memory which permits such spreading apart of the projecting walls 32, 34 without overcoming that plastic memory.

The configuration of the actuation inhibitor 10 is such that it has a height "H", and a diameter of the inside surfaces of the upstanding wall which is designated as "D". The diameter D is predetermined, as will be discussed hereafter, and the height H is also predetermined in a manner that it is typically from about 40% to about 65% of the predetermined diameter. Also, the length of the projecting walls 32, 34 is such as to be typically from about 10% to about 50% of the height H.

The predetermined diameter D is typically from about 75% to about 99% of a standardized diameter of a canister 18; more usually in the range of from about 90% to about 95% of the standardized diameter. It will be understood, of course, that in fact the diameter of aerosol medication canisters 18 that come from different manufacturers will vary, perhaps even from the same manufacturer but from lot to lot. In any event, that variation or deviance from a standardized diameter may only be very small, perhaps 1% or so.

By choosing the diameter D to be smaller to some extent than the standardized diameter of a medication canister 18, it will be seen that when the actuation inhibitor 10 is placed over the upper end of the canister 18 in the manner shown arrow 40, once the actuation inhibitor 10 is in place, it will be frictionally engaged to the outer surface of the canister 18 at the end thereof.

It will also be seen that when the actuation inhibitor 10 is placed over the end of the canister 18, particularly when it follows the path indicated by arrow 40, it will be necessary for the outwardly projecting walls 32 and 34 to flex and move away from one another, perhaps by as much as 90°. However, as noted above, the plastic memory of the semi-rigid plastics material is such as to restore, or at least attempt to restore, the configuration of the actuation inhibitor to its unstressed generally cylindrical, circular cross-section. But because the diameter D is slightly less than the diameter of the canister 18, the elastic memory of the plastics material of the aberration inhibitor 10 will set up a hoop stress within the material and thereby frictionally engage the interior walls of the actuation inhibitor 10 with the outer surface of the canister 18.

Typically, the thickness of the upstanding wall and of the outwardly projecting walls 32, 34 which comprise the actuation inhibitor 10 may be in the range of from about 10% to about 35% of the height H. The actual thickness will be chosen as a consequence of the choice of plastics material to be used, and the force which is intended to be employed to place the actuation inhibitor 10 over a canister 18, or the force which is required to overcome the effect of the friction engagement of the actuation inhibitor 10 with the canister 18 any event that it may be necessary, such as in an emergency situation where the patient requires immediate inhalation therapy.

It will also be seen by reference to arrow 42 that it is possible to place the actuation inhibitor 10 over the end of the medication canister 18 by sliding it over the end in the direction of the arrow 42.

A typical configuration of the actuation inhibitor 10 of present invention is such that its height is about 1.2 cm, the diameter is about 2.5 cm, and the thickness of the wall of the actuation inhibitor is about 0.45 cm.

Also, a typical configuration of the actuation inhibitor 10 of the present invention is such that the gap 30 extends for about 65° to about 80°, and the wall encompasses from about 280° to about 295°.

It will be understood, of course, that the present invention is directed not only to the actuation inhibitor per se, but to the combination of the actuation inhibitor 10 together with the metered dose inhaler 12 and the canister 18. It will also be understood that, in some circumstances, a patient may be in such distress that he or she will require immediate inhalation therapy and may be either in such physical or emotional distress that they are incapable of removing the actuation inhibitor 10 from the canister 18 before attempting to use the metered dose inhaler. However, such a circumstance is also accompanied by the fact that the patient may well be inclined to effect much more than the usual force to actuate the metered dose inhaler; in which case, it is possible to overcome the friction engagement of the actuation inhibitor 10 with the canister 18.

It is to be noted, however, that it has been determined that such a force is greater than that which typically occurs against the end 20 of a canister 18 as the metered dose inhaler is being jostled about in the pocket or purse of the patient, and therefore inadvertent and accidental actuation of the actuation valve of the metered dose inhaler is effectively precluded by utilization of the actuation inhibitor of the present invention.

Figure 4:
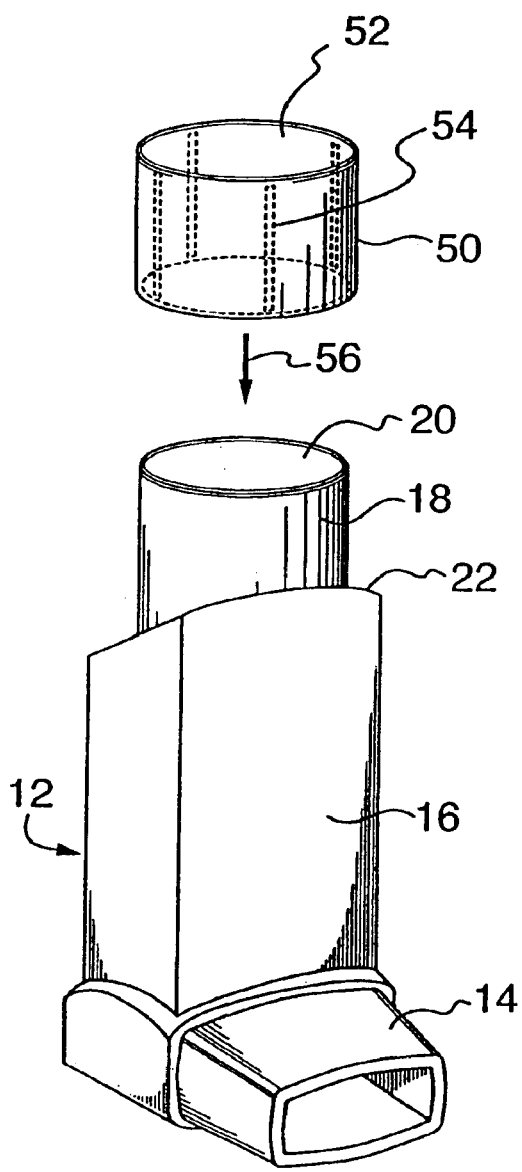
FIG. 4 is a perspective view similar to FIG. 1, but showing a different actuation inhibitor in keeping with the present invention, in its relationship to the metered dose inhaler.

Referring now to FIG. 4, a further embodiment of an actuation inhibitor for metered dose inhalers, which is in keeping with the present invention, is now described. Once again, a typical metered dose inhaler 12 is illustrated, having a canister 18 of medication in place within the housing 16.

The actuation inhibitor, in this case, takes the form of a cap 50 which is a closed cylindrical cap having a closed first end 52 at its top, and an open second end at its bottom. The cylindrical cap 50 is intended to be placed over the top end of the medication canister 18, and to fit sufficiently snugly thereto that it will not easily fall off during jostling of the metered dose inhaler as it is being carried, for example, in the purse or pocket of the patient. To that end, therefore, the inside diameter of the cylindrical cap 50 is predetermined. Also, the height of the cylindrical cap is predetermined.

As with the actuation inhibitor 10 which has been described above, the purpose of the actuation inhibitor 50 is to preclude downward movement of the medication canister 18 as it may be jostled about in the purse or pocket of the patient. Thus, when the patient wishes to administer a metered dose of the medication contained within the medication canister 18, the cylindrical cap 50 is removed—in a direction opposite to that of arrow 56, which indicates the direction of fitment of the cylindrical cap 50 to medication canister 18—and the upper end 20 of the canister 18 is depressed in usual manner.

However, in the case of an emergency where immediate administration of the medication is necessary, as has been noted above, there is sometimes a degree of panic on the part of the patient. That is, the patient becomes so aware of the requirement for medication that all other rational thoughts are foregone. The patient may, in such an emergency situation, attempt to administer the medication without first removing the cylindrical cap 50. A provision of the present invention is, however, that the cylindrical cap is made of a frangible plastics material so that, in such a situation, the cap will simply collapse or disintegrate.

On the other hand, the general strength of the cylindrical cap 50, and its fitment to the top end of a medication canister 18, is such that under normal conditions inadvertent or accidental expulsion of the medication or the propellant from the canister 18 is precluded.

To that end, the predetermined diameter of the cylindrical cap 50 may be from about 95% to about 110% of the standardized diameter of metered dose canisters which are intended for use in the metered dose inhaler. However, particularly in the event that the inside diameter of the cylindrical cap 50 is more than 100% of the standardized diameter of medication canisters, or in any event for purposes of strength for the cylindrical cap 50 in an axial direction, internal stiffening ribs 54 may be provided on the inside surface of the cylindrical cap 50.

If so, then a predetermined diameter of from about 95 percent to about 99 percent of a standardized diameter of metered dose canisters may be determined from and measured at a circle which is defined by the inner extremities of the stiffening ribs 54.

Figure 5:
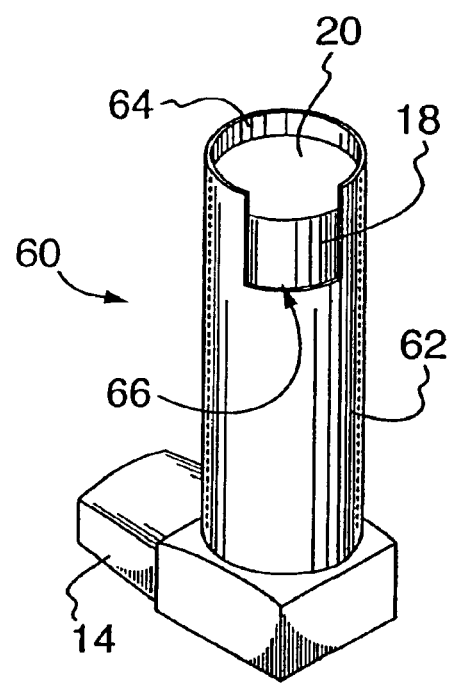
FIG. 5 is a perspective view of a metered dose inhaler in keeping with yet a further embodiment of the present invention.

Turning out FIG. 5, a further embodiment of the present invention is illustrated, but in this case it is the configuration of the L-shaped metered dose inhaler per se which is to be considered.

Here, the metered dose inhaler comprises the usual mouthpiece 14, together with a housing 62 for a conventional medication canister 18. However, it will be seen that a portion 64 of the housing 62 extends above the top surface 20 of the medication canister 18. Thus, there is less risk of the top surface 20 of the medication canister 18 being inadvertently depressed, resulting in the inadvertent or accidental loss of medication and/or propellant as a consequence of being jostled in the pocket or purse of the patient.

However, in order to permit actuation of the actuating valve at the bottom of the medication canister 18, in usual manner, a finger notch 66 is formed in the housing at a location therein which is diametrically opposed to the mouthpiece 14. Thus, medication can be administered in usual manner, as prescribed, such as by holding the metered dose inhaler supported by the thumb of the patient, with the index finger or other finger engaged with the top 20 of the medication canister 18. As the medication canister 18 is depressed against its actuating valve, the finger of the patient will move downwardly in the finger notch 66.

There has been described an actuation inhibitor for use with metered dose inhalers which is easily fitted to and removed from medication canisters but which, when in place, precludes inadvertent and accidental dispensing of the medication contained in the canister.

Other modifications may be applied. For example, a tail may be molded onto the actuation inhibitor 10 in the outer surface of the upstanding wall and location diametrically opposed to the gap 30, so as to be graspable between the thumb and finger when the actuation inhibitor is being fitted to or removed from the canister.

An alternative embodiment of actuation inhibitor for use with measured dose inhalers has been described as well. It will be understood, of course, that the frangible cylindrical cap 50 is effectively a single-use device in that, if it is depressed in an emergency situation so as to be effectively destroyed as a consequence of its frangibility, then it will have to be replaced either by another frangible cylindrical cap 50, or by a conventional actuation inhibitor 10.

It will also be understood that the alternative measured dose inhaler 60 is such that, in ordinary circumstances, once a medication canister 18 has been installed into the inhaler by having been placed in the housing 62, it is not possible to withdraw the medication canister 18 away from the measured dose inhaler 60. Accordingly, such an embodiment would be, in any event, capable of being used only in the manner that it was originally prescribed and dispensed, with the original medication and its propellant being installed in the medication canister 18.

Of course, it will be understood that the actuation inhibitor may be molded from different colors of plastics material for purposes of distinguishing one inhibition actuator from another, and so as to assist in distinguishing one inhalation medication from another. It has been noted, as well, that information, or even advertising material, can be placed on the outer surface of the actuation inhibitor, by being printed or molded thereon.

It will also be understood the use of the words "substantial" or "substantially" as well as "about" is meant to convey the meaning of reasonable but not literal exactitude. For example, substantially cylindrical conveys the meaning of being or possessing the properties of a cylinder, which is a body of rotation about an axis; and ranges that are defined with the word "about" are meant to be reasonably understood to be within engineering tolerances.

Other modifications and alterations may be used in the design and manufacture of the apparatus of the present invention without departing from the spirit and scope of the accompanying claims.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A metered dose inhaler assembly comprising in combination:
    a standardized L-shaped inhaler body;
    a metered dose canister of medication to be inhaled through the mouth of the patient; and
    an actuation inhibitor comprising an annular band of semi-rigid plastics material having a substantially cylindrical configuration with a circular cross-section;
    wherein said L-shaped inhaler comprises a mouthpiece to be place in the mouth of a patient, and a canister housing into which said metered dose canister is placed so as to have an actuating valve located near the junction of said housing and said mouthpiece;
    wherein said canister extends above said housing when in an operating, vertical orientation; and
    wherein said actuator inhibitor is removably placed over at least a portion of said canister where it extends above said housing and is frictionally engaged therewith;
    whereby, when a force is applied to said canister so is to cause the canister to attempt to move within said housing towards said junction of said housing and said mouthpiece, the frictional engagement of said actuation inhibitor with said canister will be such that there will be an interference of said actuation inhibitor with at least a portion of the end of said housing remote from said junction, so as to thereby at least initially preclude actuation of said actuation valve.

2. The actuation inhibitor assembly of claim 1, wherein said annular band of semi-rigid plastics material has an upstanding wall encompassing from about 260° to about 315°, a gap in said wall of from about 45° to about 100°, and a pair of outwardly projecting walls, one at each side of said gap;
    wherein the inside diameter of said cylindrical configuration when at rest in an unstressed manner is predetermined;
    wherein the height of said upstanding wall is from about 40% to about 65% of said predetermined diameter, and the length of each of said projecting is from about 10% to about 50% of said height;
    wherein said semi-rigid plastics material is sufficiently flexible to permit said pair of projecting walls to be spaced apart one from the other by an amount of up to about a further 90°; and
    wherein said semi-rigid plastics material has a plastic memory which permits said spreading apart of said projecting walls without overcoming said plastic memory.

3. The actuation inhibitor assembly of claim 2, wherein said predetermined diameter is from about 75% to about 99% of a standardized diameter of the metered dose canisters intended for use in metered dose inhalers.

4. The actuation inhibitor assembly of claim 2, wherein the thickness of said upstanding wall and of said outwardly projecting walls is in the range of from about 10% to about 35% of the height thereof.

5. The actuation inhibitor assembly of claim 2, wherein said outwardly projecting walls are substantially parallel one to the other.

6. The actuation inhibitor assembly of claim 2, wherein said outwardly projecting walls extend radially outwardly from the respective sides of said gap.

7. The actuation inhibitor assembly of claim 2, wherein said gap extend for about 65° to about 80°, and said wall encompasses from about 280° to about 295°.

8. The actuation inhibitor assembly of claim 2, wherein said predetermined diameter is from about 90% to a out 95% of a standardized diameter of metered dose canisters intended for use in metered dose inhalers.

9. The assembly of claim 1, wherein the predetermine diameter of said actuation inhibitor, before is frictional engagement with said canister, is about 90% to about 95% of the diameter of said canister.

10. A method of preventing accidental actuation of a metered dose inhaler comprising a standardized L-shaped inhaler body, a mouthpiece to be placed in the mouth of a patient, a metered dose canister of medication to be inhaled through the mouth of the patient, and a canister housing into which said canister is placed so is to have an actuating valve located near the junction of said housing and said mouthpiece, said canister extending above said housing when in an operating, vertical orientation, said method comprising:
    temporarily placing an actuation inhibitor comprising an annular band of semi-rigid plastics material having a substantially cylindrical configuration with a circular cross-section over at least a portion of said canister such that said actuation inhibitor extends above said housing and is frictionally engaged therewith;
    whereby, when a force is applied to said canister so as to cause the canister to attempt to move within said housing towards said junction of said housing and said mouthpiece, the frictional engagement of said actuation inhibitor with said canister is such that there is interference of said actuation inhibitor with at least a portion of the end of said housing remote from said junction, so as to thereby at least initially preclude actuation of said actuation valve.

11. The method of claim 10, wherein said annular band of semi-rigid plastics material has an upstanding wall encompassing from about 260° to about 315°, a gap in said wall of from about 45° to about 100°, and a pair of outwardly projecting walls, one at each side of said gap; wherein the inside diameter of said cylindrical configuration when at rest in an unstressed manner is predetermined; wherein the height of said upstanding wall is from about 40% to about 65% of said predetermined meter, and the length of each of said projecting walls is from about 10% to about 50% of said height; wherein said actuation inhibitor is placed over said portion of said canister by spreading apart said projecting walls.

* * * * *